(12) United States Patent
Baier et al.

(10) Patent No.: US 6,268,210 B1
(45) Date of Patent: Jul. 31, 2001

(54) SANDWICH ARRAYS OF BIOLOGICAL COMPOUNDS

(75) Inventors: Joerg Baier, Foster City; Brian Hauser, Campbell; Radoje T. Drmanac, Palo Alto, all of CA (US)

(73) Assignee: Hyseq, Inc., Sunnyvale, CA (US)

( * ) Notice: Subject to any disclaimer, the term of this patent is extended or adjusted under 35 U.S.C. 154(b) by 0 days.

(21) Appl. No.: 09/251,303

(22) Filed: Feb. 17, 1999

Related U.S. Application Data

(63) Continuation-in-part of application No. 09/085,529, filed on May 27, 1998, now abandoned.
(60) Provisional application No. 60/111,761, filed on Dec. 11, 1998.

(51) Int. Cl.⁷ .............................. C12M 1/34; C12Q 1/68; G01N 21/00
(52) U.S. Cl. ..................... 435/288.5; 435/288.4; 435/287.2; 435/287.3; 435/6; 422/50; 422/58
(58) Field of Search .................. 422/50, 58; 435/287.2, 435/6, 288.4, 288.5, 287.3

(56) References Cited

U.S. PATENT DOCUMENTS

| | | |
|---|---|---|
| 5,445,934 | 8/1995 | Fodor et al. |
| 5,525,464 | 6/1996 | Drmanac et al. ............ 435/6 |
| 5,744,305 | 4/1998 | Fodor et al. ............... 435/6 |
| 5,763,263 * | 6/1998 | Dehlinger ................ 435/287 |
| 5,807,522 * | 9/1998 | Brown et al. ............. 422/50 |
| 5,843,767 | 12/1998 | Beattie ................. 435/287.1 |

FOREIGN PATENT DOCUMENTS

| | | |
|---|---|---|
| WO 95/09248 | 4/1995 | (WO) . |
| WO 98/31836 | 7/1998 | (WO) . |

* cited by examiner

Primary Examiner—W. Gary Jones
Assistant Examiner—B J Forman
(74) Attorney, Agent, or Firm—Marshall, O'Toole, Gerstein, Murray & Borun

(57) ABSTRACT

The present invention relates to spatially-addressable sandwich arrays of compounds, particularly biological compounds such as peptides and polynucleotide probes, and methods of making and using the same. The present invention also relates to a method and device for holding together the substrates of the sandwich array, more particularly, a clamping device for securely yet safely holding substrates of a sandwich array together during assembly, use, storage, and/or transport of the sandwich array.

21 Claims, 6 Drawing Sheets

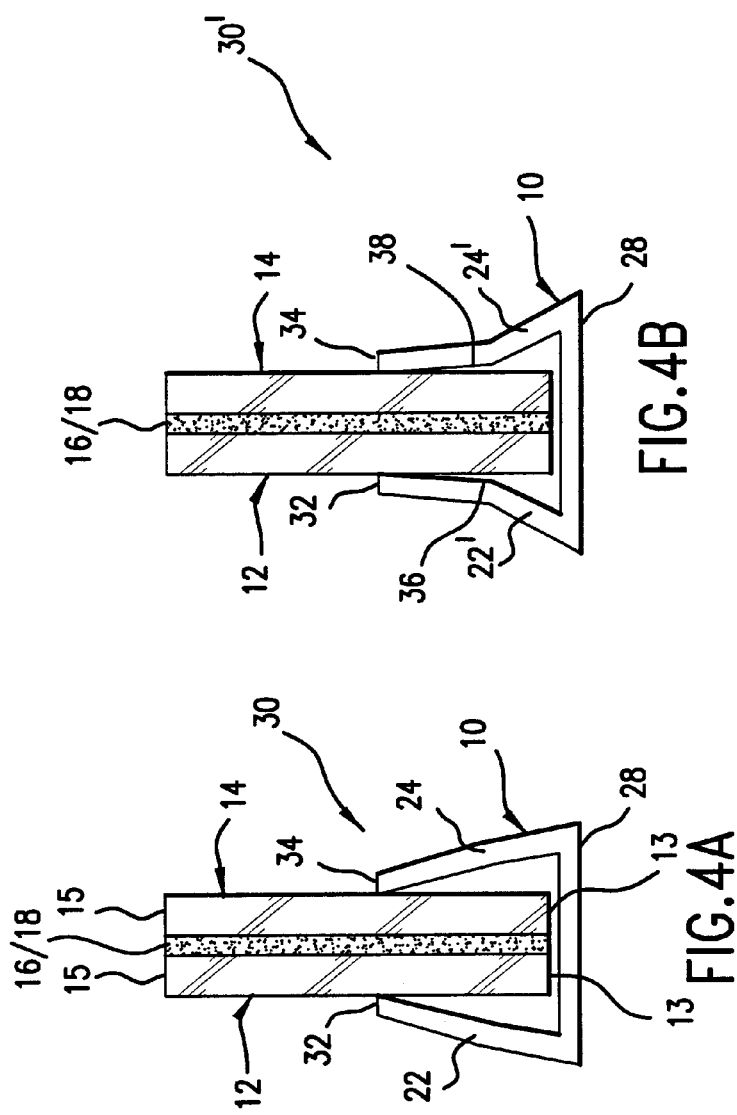
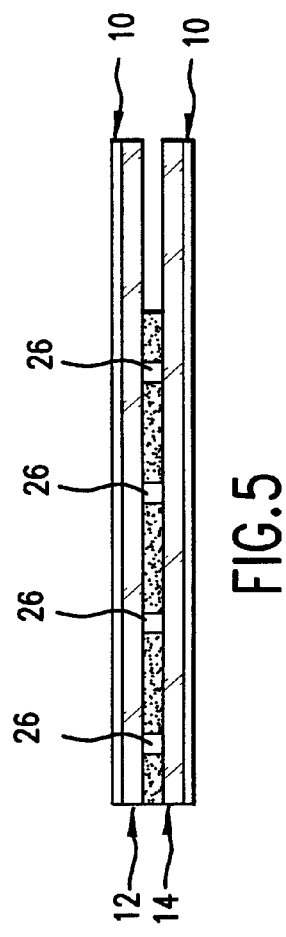

SANDWICH ARRAYS OF BIOLOGICAL COMPOUNDS

This application is a continuation-in-part of U.S. application Ser. No. 09/085,529 filed May 27, 1998, now abandoned and claims benefit of Provisional U.S. application Ser. No. 60/111,761, filed Dec. 11, 1998.

Related applications include; U.S. application Ser. No. 08/959,365, filed Oct. 28, 1997, now abandoned; U.S. application Ser. No. 08/947,779, filed Oct. 9, 1997; U.S. application Ser. No. 08/912,885, filed Aug. 15, 1997; U.S. application Ser. No. 08/892,503, filed Jul. 14, 1997; U.S. application Ser. No. 08/812,951, filed Mar. 4, 1997; and U.S. application Ser. No. 08/784,747, filed Jan. 16, 1997. The disclosures of all of the above related applications are incorporated by reference herein in their entireties.

FIELD OF THE INVENTION

The present invention relates to spatially-addressable sandwiched arrays of compounds, particularly biological compounds such as peptides and polynucleotide probes, and methods of making and using the same. The present invention also relates to a method and device for holding together the individual components composing the sandwich array, more particularly, a clamping device for securely yet safely holding substrates of a sandwich array together during assembly, use, storage, and/or transport of the sandwich array.

BACKGROUND OF THE INVENTION

Recent advances in the ability to construct arrays of biological compounds have greatly facilitated the ease and speed with which certain biological assays can be performed. For example, in the areas of nucleic acid sequencing and analysis, the advent of new technologies for constructing arrays of immobilized target nucleic acids or oligonucleotide probes has enabled the rapid screening and sequencing of nucleic acids. Arrays of peptides and small biomolecules have also proven useful in binding assays used in pharmaceutical development. The usefulness of these arrays depends on the ability to generate and use arrays with spatially addressable regions of defined composition or sequence.

Several technologies have been developed for producing such arrays. For example, several researchers have devised methods for in situ synthesis of arrays of biological polymers, such as nucleic acids, peptides, and carbohydrates. These methods use, for example, physical barriers to separate different synthesis sites, devices (such as inkjet printers) for precise delivery of reagents to different synthesis sites, or masking techniques that allow the use of light to determine the course of synthesis. See, e.g., WO 90/03382; Fodor et al., 1991, Science 251:767–73; Pease et al., 1994, Proc. Natl. Acad. Sci. 91:5022–26; U.S. Pat. No. 5,424,186, to Fodor et al. Alternatively, presynthesized biological compounds or biological polymers may be attached directly to the substrate at precise positions using a variety of techniques, ranging from simple spotting to robotic delivery systems. A variety of different substrates and techniques for attaching the biological compounds to the substrates are also available.

As noted above, arrays of nucleic acids have proven particularly valuable. The ability to perform many previously available techniques has been greatly enhanced by the availability of arrays, which permit many assays to be performed simultaneously, rather than having to do each assay individually. Other techniques that would have been virtually impossible are now possible using polynucleotide arrays.

One technique that has been particularly enhanced by the availability of arrays of nucleic acids is sequencing by hybridization (SBH). SBH is a technique for rapidly sequencing nucleic acids without using gels. In SBH, polynucleotides having overlapping sequences are hybridized to a target nucleic acid. The sequences of the polynucleotides that hybridized are determined and their common sequences overlapped to generate the sequence of the target nucleic acid. The use of arrays has allowed the generation of sufficient hybridization information to make SBH feasible on a large scale.

SBH is divided into three formats, depending on the nature of the array and the way in which it is interrogated. In Format I, an immobilized target nucleic acid is interrogated with labeled solution-phase polynucleotide probes. In Format II, a spatially-addressable array of immobilized polynucleotide probes is interrogated with a labeled solution-phase target nucleic acid. In Format III, an array of immobilized polynucleotide probes is hybridized with an unlabeled solution-phase target nucleic acid and one or more labeled solution-phase oligonucleotide probes. Hybridization is assayed by ligating the labeled oligonucleotide probes to the immobilized polynucleotides. All three formats require the ability to distinguish perfectly matched hybrids from hybrids that contain a single mismatch at any position. For a more detailed discussion of SBH and the three formats, see WO 98/31836, particularly at pages 1–3.

While the availability of high-density arrays of immobilized compounds has revolutionized the speed with which certain biological assays can be performed, array-based assays still suffer from drawbacks. Samples are often available in limited amounts, which are incompatible with the large volumes of assay solutions required to immerse the arrays. Thus, there remains a need in the art for improved arrays that allow the use of small volumes of assay solutions.

SUMMARY OF THE INVENTION

These and other shortcomings in the art are overcome by the present invention, which in one aspect provides spatially addressable sandwich arrays of immobilized compounds. In the sandwich arrays, two or more substrates each having a spatially addressable array of compounds immobilized thereon are combined into "sandwiches" in which the individual arrays are separated by spacer regions. The spacers may be, for example, masks made of TEFLON or other similar, preferably hydrophobic and preferably nonabsorbent, material which may be provided on one or more of the substrates. The masks are designed so that so that when the substrates are pressed together, the masks form at least one reaction chamber with walls defined by the masks and the substrates. Preferably, a plurality of spacers is provided to separate a plurality of arrays on a single substrate; these arrays may be different or may be replicates. The plurality of spacers forms a plurality of chambers in the sandwich array, with each chamber designed to contain a small volume of assay solution. In order to form the desired chamber or chambers, the substrates should be maintained in a fixed position with respect to each other, such as by a holder. Advantageously, the sandwich arrays of the present invention allow two or more compound arrays to be interrogated simultaneously with very small volumes of assay solution.

In a preferred embodiment, the immobilized compounds are immobilized nucleic acid compounds, particularly polynucleotides. However, peptides, proteins, small organic compounds (such as drug candidates), carbohydrates, or any of a variety of other compounds that can be arrayed on a substrate may all be used in the sandwich arrays of the present invention.

In use, the plurality of substrates with a plurality of arrays of compounds attached thereto are held together such that the substrates and spacers form one or more chambers, with the compounds of the arrays exposed inside the chamber or chambers. Assay solution or solutions is added to the chamber or chambers, where it contacts the arrays. The arrays and assay solution(s) are maintained in contact under the desired conditions for the desired time (depending on the requirements of the particular assay being performed). The assay solution(s) is removed. The arrays are optionally washed and separated, or separated and washed. The results of the assay are then determined.

In addition to the sandwich arrays of the present invention, a device is provided for holding together a pair of substrates of a sandwich array and also for serving other desired functions desired during the use of the sandwich array. The device includes a preferably slidable clamping bar having clamping arms biased together to provide sufficient force to securely clamp together the substrates without damaging the substrates. The clamping bar preferably prevents leakage of the solution to be tested, such as by extending across at least the bottom edge. Moreover, the clamping bar preferably has a flat bottom surface to facilitate positioning of the sandwich array in a desired substantially upright orientation for filling. A second clamping bar may be positioned over the end of the substrates opposite the end over which the first clamping bar has been positioned. The clamping walls of the clamping bars of the present invention are preferably dimensioned so that once clamping bars have been positioned over opposite edges of the substrates, the walls of the clamping bars cover substantially the entire substrate. Accordingly, the clamping bars of the present invention preferably serve a dual function of holding the substrates together to form the filling chambers and also of providing a protective holding device for storage or shipping of the sandwich array. The clamping bar of the present invention is easily removable from the substrates to permit separation of the substrates as desired.

The above and other features and advantages of the present invention will be readily apparent from the following detailed description of the invention, the scope of the invention being set out in the appended claims.

BRIEF DESCRIPTION OF THE FIGURES

The detailed description will be better understood in conjunction with the accompanying drawings, wherein like reference characters represent like elements, as follows:

FIG. 4A is a cross-sectional view along line IV—IV of the sandwich array and clamping bar of FIG. 2, and 4B is a similar view of an alternative embodiment of the clamping bar;

FIG. 5 is a top cross-sectional view along line V—V of the sandwich array and clamping bar of FIG. 2;

DETAILED DESCRIPTION OF THE INVENTION

Definitions

Figure 1A:
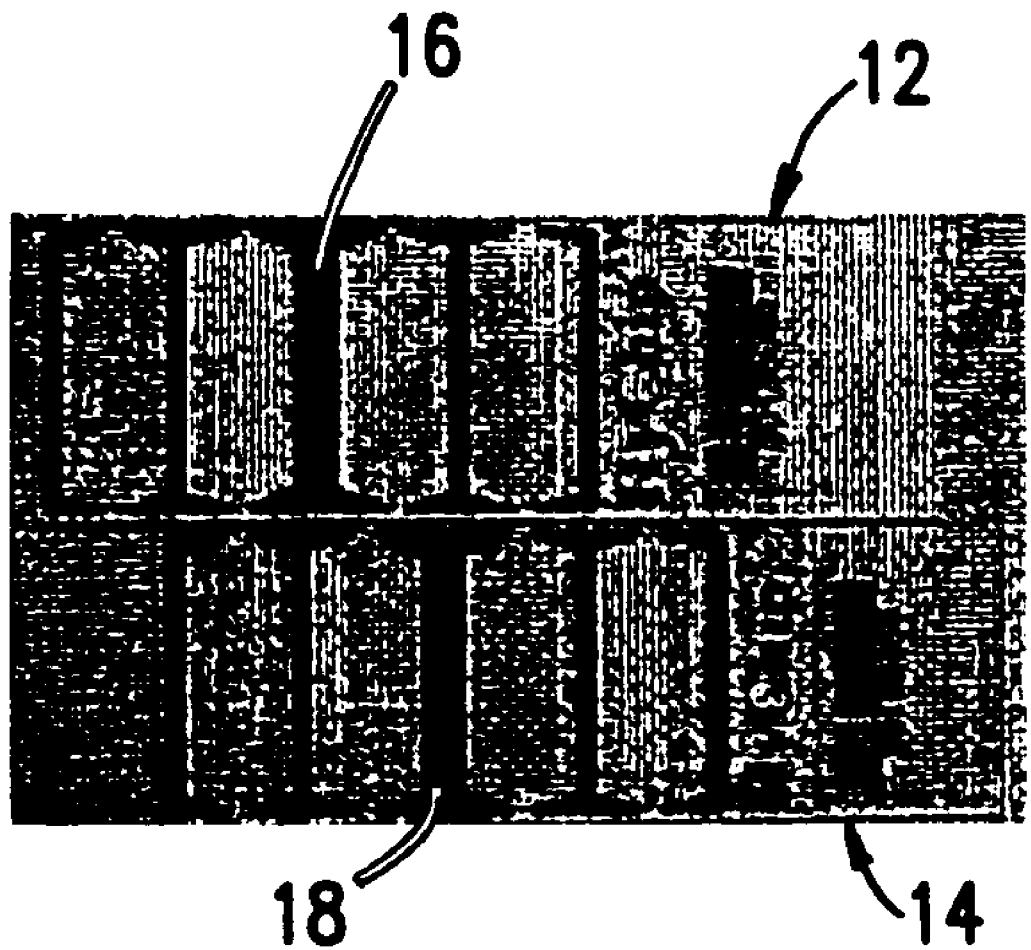
FIG. 1 is a photographic (A) or drawn (B) plan view of a pair of substrates with spacers formed thereon, the substrates and masks being configured for coupling together to form a sandwich array.

As used herein, the following terms shall have the following meanings:

"Spatially addressable array" refers to an array in which each element or component of the array is identifiable by its spatial address, for example its xyz coordinates. Spatially addressable arrays according to the invention can be one dimensional, for example a linear array; two dimensional; or three dimensional. Preferably, the spatially addressable arrays are two dimensional.

"Spacer" refers to a material disposed between and holding separate two or more arrays in a sandwich array. Spacers may be used to define one or more chambers between the arrays that make up the sandwich. Spacers are preferably made from a hydrophobic, preferably nonabsorbent, material, for example TEFLON or silicon, or other materials well known in the art or described in WO 95/09248.

"Address" or "spot" refers to a particular position in an array. Each address or spot has unique xyz coordinates. The structure of a compound immobilized at a particular address or spot is definable by its coordinates.

"Polynucleotide" refers to a nucleic acid sequence which is immobilized on a substrate. The polynucleotides of the present invention can contain as few as four bases or as many as several hundred or more bases. The polynucleotides can be composed of natural or modified bases or combinations thereof, and can contain one or more modified interlinkages.

"Target nucleic acid" refers to a nucleic acid of known or unknown sequence to be analyzed. The target nucleic acid can be virtually any number of nucleotides in length, but typically is longer than the polynucleotides of the array.

The Invention

The problems in the art discussed in the Background section are solved by the present invention. The use of multiple arrays in a sandwich configuration, as presently described, allows more efficient and effective interrogation of arrays of compounds. These sandwich arrays increase efficiency by allowing multiple arrays to be assayed simultaneously, with one small-volume probe mixture. Additionally, particularly in the context of hybridization to arrays of nucleic acids, the sandwich configuration may improve the reaction kinetics of the assay. The invention is also directed to the use of sandwich arrays in various assay techniques, as well as to holders for the sandwich arrays.

The present sandwich arrays may be used with a wide variety of different types of compounds that may be immobilized in arrays. The sandwich arrays are particularly exemplified herein in terms of polynucleotides immobilized on a substrate, but they are equally applicable to other types of compounds. For example, one of skill in the art could easily adapt the present sandwich arrays to apply to other nucleic acids (both DNA and RNA), peptides, polypeptides, proteins, carbohydrates, small biological compounds (e.g. drug candidates), or any other type of compound that can be immobilized on a substrate by any method. Preferably, the compound is a nucleic acid, particularly DNA or RNA, and especially a polynucleotide.

The individual arrays of the present invention may be of any desired size, from two immobilized compounds to $10^6$ immobilized compounds or even more. The size of the underlying substrate is one factor in determining the size of the array. The upper and lower limits on the size of the substrate are determined solely by the practical considerations of working with extremely small or large substrates. For a given substrate size, the upper limit is determined only by the ability to create and detect the immobilized compounds in the array. The preferred number of immobilized compounds on an array generally depends on the particular use to which the array is to be put. For example, sequencing by hybridization will generally require large arrays, while mutation detection may require only a small array. In general, preferred arrays contain from 2 to about $10^6$ immobilized compounds, more preferably from about 100 to about $10^5$ immobilized compounds, even more preferably from about 400 to about $10^4$ immobilized compounds, and most preferably from about 500 and about 2000 immobilized compounds. Furthermore, not all immobilized compounds on the array need be unique. Indeed, in many applications, redundancies in the immobilized compounds are desirable for the purposes of acting as internal controls.

A variety of techniques have been described for synthesizing and/or immobilizing arrays of polynucleotides, including in situ synthesis, where the polynucleotides are synthesized directly on the surface of the substrate (see, e.g., U.S. Pat. No. 5,744,305 to Fodor, et al.,) and attachment of pre-synthesized polynucleotides to the surface of a substrate at discrete locations (see, e.g., WO 98/31836). Additional methods are described in WO 98/31836 at pages 41–45 and 47–48, among other places. The present invention is suitable for use with any of these currently available, or later developed, techniques. Additionally, methods for normalizing different quantities of compounds immobilized at each spot, such as those described in provisional U.S. application Ser. No. 60/111,761, filed Dec. 11, 1998, may be advantageously used in the context of the present invention.

Moreover, while the in situ synthesis method is commonly described utilizing phosphoramidite reagents, it will be recognized that other reagents utilizing other synthesis strategies can also be employed, and in certain circumstances may be preferable. Non-limiting examples of suitable chemistries and reagents are described, for example in Oligonucleotide Synthesis: A Practical Approach, M. J. Gait, Ed., IRL Press, Oxford, England, 1985.

The compounds of the arrays of the invention are immobilized on a solid substrate. The nature and geometry of the solid substrate will depend upon a variety of factors, including, among others, the type of array (e.g., one-dimensional, two-dimensional or three-dimensional; in the context of the present invention, two-dimensional arrays are preferred); the mode of attachment (e.g., covalent or non-covalent); and the physical requirements of the sandwich format. Generally, the substrate can be composed of any material which will permit immobilization of the polynucleotide (or other compound) and which will not melt or otherwise substantially degrade under the conditions used to hybridize and/or denature nucleic acids. In addition, where covalent immobilization is contemplated, the substrate should be activatable with reactive groups capable of forming a covalent bond with the polynucleotide to be immobilized. Preferably, the individual arrays are two-dimensional arrays covalently immobilized on a relatively inflexible substrate.

A number of materials suitable for use as substrates in the instant invention have been described in the art. Exemplary suitable materials include, for example, acrylic, styrene-methyl methacrylate copolymers, ethylene/acrylic acid, acrylonitrile-butadiene-styrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6-6, nylon 6/9, nylon 6/10, nylon 6/12, nylon 11 and nylon 12), polycarylonitrile (PAN), polyacrylate, polycarbonate, polybutylene terephthalate (PBT), polyethylene terephthalate (PET), polyethylene (including low density, linear low density, high density, cross-linked and ultra-high molecular weight grades), polypropylene homopolymer, polypropylene copolymers, polystyrene (including general purpose and high impact grades), polytetrafluoroethylene (PTFE), fluorinated ethylene-propylene (FEP), ethylene-tetrafluoroethylene (ETFE), perfluoroalkoxyethylene (PFA), polyvinyl fluoride (PVF), polyvinylidene fluoride (PVDF), polychlorotrifluoroethylene (PCTFE), polyethylene-chlorotrifluoroethylene (ECTFE), polyvinyl alcohol (PVA), silicon styrene-acrylonitrile (SAN), styrene maleic anhydride (SMA), metal oxides and glass.

The substrate is preferably in the form of sheets, and may be permeable or impermeable, depending on the type of array. A relatively inflexible, impermeable substrate such as glass or plastic is preferred. For two-dimensional arrays, the substrate is preferably in the form of plastic or glass sheets in which at least one surface is substantially flat. Particularly preferred substrates for use with two-dimensional arrays are glass slides.

The composition of the immobilized polynucleotides is not critical. The only requirement is that they be capable of hybridizing to a target nucleic acid of complementary sequence. For example, the polynucleotides may be composed of all natural or all synthetic nucleotide bases, or a combination of both. Non-limiting examples of modified bases suitable for use with the instant invention are described, for example, in Practical Handbook of Biochemistry and Molecular Biology, G. Fasman, Ed., CRC Press, 1989, pp. 385–392. While in most instances the polynucleotides will be composed entirely of the natural bases (A, C, G, T or U), in certain circumstances the use of synthetic bases may be preferred.

Moreover, while the backbones of the polynucleotides will typically be composed entirely of "native" phosphodiester linkages, they may contain one or more modified linkages, such as one or more phosphorothioate, phosphoramidite or other modified linkages. As a specific example, one or more immobilized polynucleotides may be a peptide nucleic acid (PNA), which contains amide interlinkages. Additional examples of modified bases and backbones that can be used in conjunction with the invention, as well as methods for their synthesis can be found, for example, in Uhlman & Peyman, 1990, Chemical Review 90(4):544–584; Goodchild, 1990, Bioconjugate Chem. 1(3):165–186; Egholm et al., 1992, J. Am. Chem. Soc. 114:1895–1897; Gryaznov et al., J. Am. Chem. Soc. 116:3143–3144, as well as the references cited in all of the above.

While the immobilized polynucleotides will in most instances be a contiguous stretch of nucleotides, they need not be. Stretches of nucleotides can be interrupted by one or more linker molecules that do not participate in sequence-specific base pairing interactions with a target nucleic acid. The linker molecules may be flexible, semi-rigid or rigid, depending on the desired application. A variety of linker molecules useful for spacing one compound from another or from a solid surface have been described in the art (and are described more thoroughly infra); all of these linker molecules can be used to space regions of immobilized polynucleotides from one another. In a preferred embodiment of this aspect of the invention, the linker moiety is from one to ten, preferably one to six, alkylene glycol moieties, preferably ethylene glycol moieties.

The immobilized polynucleotides may be as few as four, or as many as hundreds, or even more, nucleotides in length. Specifically contemplated as polynucleotides according to the invention are nucleic acids that are typically referred to in the art as oligonucleotides and also those referred to as nucleic acids. Thus, the arrays of the present invention are useful not only in applications where target nucleic acids are hybridized to immobilized arrays of relatively short (i.e., 6–20 nucleotide) polynucleotide probes (such as format II SBH), but also in applications where relatively short polynucleotide probes are hybridized to arrays of immobilized nucleic acids.

The polynucleotides of the array can be of any desired sequence. In a preferred embodiment, they can comprise all possible polynucleotides of a given length k, which would result in an array of $4^k$ unique elements. For all polynucleotides of, for example, 6 bases in length, the sequences would comprise an array with 4096 unique elements. Alternatively, the polynucleotides can make up the "universal set" for sequencing a nucleic acid, as discussed in WO 98/31836, particularly pages 27–29.

In an alternative embodiment, the set of polynucleotides may correspond to particular mutations that are to be identified in a known sequence. For example, if a particular nucleic acid is known to contain an unidentified mutation at a particular position, then the mutated position can be identified with an array of eight polynucleotides, three corresponding to the three possible substitutions at that position, one corresponding to the deletion of the base at that position, and four corresponding to the insertion of the four possible bases at that position. Alternatively, for a known gene that may contain any of several possible identified mutations, the array can comprise polynucleotides corresponding to the different possible mutations. This embodiment is particularly useful for genes like oncogenes and tumor suppressors, which frequently have a variety of known mutations in different positions. Using arrays facilitates determining whether or not these genes contain mutations by allowing simultaneous screening with polynucleotides corresponding to each of these different positions.

In another alternative embodiment, each spot of the array can comprise a mixture of polynucleotides of different sequences. These mixtures may comprise degenerate polynucleotides of the structure $N_xB_yN_z$, wherein N represents any of the four bases and varies for the polynucleotides in a given mixtures, B represents any of the four bases but is the same for each of the polynucleotides in a given mixture, and x, y, and z are integers. The number of known bases y defines the "information content" of the polynucleotide, since the degenerate ends do not contribute to the information content of the probes. Arrays comprising this type of mixture are useful in, for example, sequencing by hybridization. Hybridization discrimination of mismatches in these degenerate probe mixtures refers only to the length of the informational content, not the full physical length.

Alternatively, the spots may comprise mixtures of polynucleotides that correspond to different regions of a known nucleic acid; these regions may be overlapping, adjacent, or nonadjacent. Arrays comprising these types of mixtures are useful in, for example, identifying specific nucleic acids, including those from particular pathogens or other organisms. Both types of mixtures are discussed in WO 98/31836, particularly at pages 123–128.

The polynucleotides can be isolated from biological samples, generated by PCR reactions or other template-specific reactions, or made synthetically. Methods for isolating polynucleotides from biological samples and/or PCR reactions are well-known in the art, as are methods for synthesizing and purifying synthetic polynucleotides. Probes isolated from biological samples and/or PCR reactions may, depending on the desired mode of immobilization, require modification at the 3'- or 5'-terminus, or at one or more bases, as will be discussed more thoroughly below. Moreover, since the polynucleotide must be capable of hybridizing to a target nucleic acid, if not already single stranded, it should preferably be rendered single stranded, either before or after immobilization on the substrate.

The polynucleotides can be immobilized on the substrate using a wide variety of techniques. For example, the polynucleotides can be adsorbed or otherwise non-covalently associated with the substrate (for example, immobilization to nylon or nitrocellulose filters using standard techniques); they may be covalently attached to the substrate; or their association may be mediated by specific binding pairs, such as biotin and streptavidin. Of these methods, covalent attachment is preferred.

In order to effect covalent attachment, the substrate must first be activated, i.e., treated so as to create reactive groups on or within the substrate that can react with a reactive group on the polynucleotide to form a covalent linkage. Those of skill in the art will recognize that the desired reactive group will depend on the chemistry used to attach the polynucleotides to the substrate and the composition of the substrate. Typical reactive groups useful for effecting covalent attachment of polynucleotides to substrates include hydroxyl, sulfonyl, amino, epoxy, isothiocyanate and carboxyl groups; however, other reactive groups as will be apparent to those having skill may also be used and are also included within the scope of the invention.

For a review of the myriad techniques that can be used to activate the substrates with suitable reactive groups, see Wiley Encyclopedia of Packaging Technology, 2d Ed., Brody & Marsh, Ed., "Surface Treatment," pp. 867–874, John Wiley & Sons (1997), and the references cited therein (hereinafter "Surface Treatment"). Chemical methods suitable for generating amino groups on silicon oxide substrates are described in Atkinson & Smith, "Solid Phase Synthesis of Oligodeoxyribonucleotides by the Phosphite Triester Method," In: Oligonucleotide Synthesis: A Practical Approach, M J Gait, Ed., 1984, IRL Press, Oxford, particularly at pp. 45–49 (and the references cited therein); chemical methods suitable for generating hydroxyl groups on silicon oxide substrates are described in Pease et al., 1994, Proc. Natl. Acad. Sci. USA 91:5022–5026 (and the references cited therein); chemical methods for generating functional groups on polymers such as polystyrene, polyamides and grafted polystyrenes are described in Lloyd-Williams et al., 1997, Chemical Approaches to the Synthesis of Peptides and Proteins, Chapter 2, CRC Press, Boca Raton, Fla. (and the references cited therein).

Those of skill in the art will recognize that in embodiments employing covalent attachment, the covalent bond formed between the polynucleotide and the substrate must be substantially stable to the various conditions under which the array will be assayed, to avoid loss of polynucleotide during the assay. One such stable bond is the phosphodiester bond, which connects the various nucleotides in a polynucleotide, and which can be conveniently formed using well-known chemistries (see, e.g., Oligonucleotide Synthesis: A Practical Approach, 1984, supra). Other stable bonds suitable for use with hydroxyl-activated substrates include phosphorothioate, phosphoramidite, or other modified nucleic acid interlinkages. For substrates modified with amino groups, the bond could be a phosphoramidate, amide or peptide bond. When substrates are activated with epoxy functional groups, a stable C—N bond could be formed. Suitable reagents and conditions for forming such stable bonds are well known in the art. Other stable bonds suitable for use with the arrays of the invention will be apparent to those of skill in the art.

In embodiments in which pre-synthesized polynucleotides are covalently attached to the substrate, the polynucleotides may be via their 3'-terminus, 5'-terminus or by way of a reactive group at one of the bases. Synthesis supports and synthesis reagents useful for modifying the 3'- and/or 5'-terminus of synthetic polynucleotides, or for incorporating a base modified with a reactive group into a synthetic polynucleotide, are well-known in the art and are also commercially available.

For example, methods for synthesizing 5'-modified polynucleotides are described in Agarwal et al., 1986, Nucl. Acids Res. 14:6227–6245 and Connelly, 1987, Nucl. Acids Res. 15:3131–3139. Commercially available products for synthesizing 5'-amino modified polynucleotides include the N-TFA-C6-AminoModifer™, N-MMT-C6-AminoModifer™ and N-MMT-C12-AminoModifier™ reagents available from Clontech Laboratories, Inc., Palo Alto, Calif.

Methods for synthesizing 3'-modified polynucleotides are described in Nelson et al., 1989, Nucl. Acids Res. 17:7179–7186 and Nelson et al., 1989, Nucl. Acids Res. 17:7187–7194. Commercial products for synthesizing 3'-modified polynucleotides include the 3'-Amino-ON™ controlled pore glass and Amino Modifier II™ reagents available from Clontech Laboratories, Inc., Palo Alto, Calif.

Other methods for modifying the 3' and/or 5' termini of polynucleotides, as well as for synthesizing polynucleotides containing appropriately modified bases are provided in Goodchild, 1990, Bioconjugate Chem. 1:165–186, and the references cited therein. Chemistries for attaching such modified polynucleotides to substrates activated with appropriate reactive groups are well-known in the art (see, e.g., Ghosh & Musso, 1987, Nucl. Acids Res. 15:5353–5372; Lund et al., 1988, Nucl. Acids Res. 16:10861–10880; Rasmussen et al., 1991, Anal. Chem. 198:138–142; Kato & Ikada, 1996, Biotechnology and Bioengineering 51:581–590; Timofeev et al., 1996, Nucl. Acids Res. 24:3142–3148; O'Donnell et al., 1997, Anal. Chem. 69:2438–2443).

Methods and reagents for modifying the ends of polynucleotides isolated from biological samples and/or for incorporating bases modified with reactive groups into nascent polynucleotides are also well-known and commercially available. For example, an isolated polynucleotide can be phosphorylated at the 5'-terminus with phosphorokinase and this phosphorylated polynucleotide covalently attached to an amino-activated substrate through a phosphoramidate or phosphodiester linkage. Other methods will be apparent to those of skill in the art.

In one convenient embodiment, pre-synthesized polynucleotides, modified at their 3'- or 5'-termini with a primary amino group, are conjugated to a carboxy-activated substrate. Chemistries suitable for forming carboxamide linkages between carboxyl and amino functional groups are well-known in the art of peptide chemistry (see, e.g., Atherton & Sheppard, Knorr et al., 1989, Tet. Lett. 30(15):1927–1930; Bannworth & Knorr, 1991, Tet. Lett. 32(9):1157–1160; and Wilchek et al., 1994, Bioconjugate Chem. 5(5):491–492; Solid Phase Peptide Synthesis, 1989, IRL Press, Oxford, England and Lloyd-Williams et al., Chemical Approaches to the Synthesis of Peptides and Proteins, 1997, CRC Press, Boca Raton, Fla. and the references cited therein). Any of these methods can be used to conjugate amino-modified polynucleotides to a carboxy-activated substrate.

In another convenient embodiment, the polynucleotides are synthesized directly on a hydroxy-activated substrate using commercially available phosphoramidites synthesis reagents. In this mode, the polynucleotides are covalently attached to the substrate via their 3'-termini by way of a phosphodiester linkage. Alternatively, photoprotected phosphoramidites and the photolithographic methods described in U.S. Pat. No. 5,744,305 to Fodor et al. and Pease et al., 1994, supra, can be used.

Whether synthesized directly on the activated substrate or immobilized on the activated substrate after synthesis or isolation, the polynucleotides can optionally be spaced away from the substrate by way of one or more linkers. As will be appreciated by those having skill in the art, such linkers will be at least bifunctional, i.e., they will have one functional group or moiety capable of forming a linkage with the activated substrate and another functional group or moiety capable of forming a linkage with another linker molecule or the polynucleotides. The linkers may be long or short, flexible or rigid, charged or uncharged, hydrophobic or hydrophilic, depending on the particular application.

In certain circumstances, such linkers can be used to "convert" one functional group into another. For example, an amino-activated substrate can be converted into a hydroxyl-activated substrate by reaction with, for example, 3-hydroxy-propionic acid. In this way, substrate materials which cannot be readily activated with a specified reactive functional group can be conveniently converted into an appropriately activated substrate. Chemistries and reagents suitable for "converting" such reactive groups are well-known, and will be apparent to those having skill in the art.

Linkers can also be used, where necessary, to increase or "amplify" the number of reactive groups on the activated substrate. For this embodiment, the linker will have three or more functional groups. Following attachment to the activated substrate by way of one of the functional groups, the remaining two or more groups are available for attachment of polynucleotides. Amplifying the number of functional groups on the activated substrate in this manner is particularly convenient when the substrate cannot be readily activated with a sufficient number of reactive groups.

Reagents for amplifying the number of reactive groups are well-known and will be apparent to those of skill in the art. A particularly convenient class of amplifying reagents are the multifunctional epoxides sold under the trade name DENACOL™ (Nagassi Kasei Kogyo K.K.). These epoxides contain as many as four, five, or even more epoxy groups, and can be used to amplify substrates activated with reactive groups that react with epoxides, including, for example, hydroxyl, amino and sulfonyl activated substrates. The resulting epoxy-activated substrate can be conveniently converted to a hydroxyl-activated substrate, a carboxy-activated substrate, or other activated substrate by well-known methods.

Linkers suitable for spacing biological compounds such as polynucleotides from solid surfaces are well-known in the art, and include, by way of example and not limitation, polypeptides such as polyproline or polyalanine, saturated or unsaturated bifunctional hydrocarbons such as 1-aminohexanoic acid, polymers such as polyethylene glycol, etc. 1,4-Dimethoxytrityl-polyethylene glycol phosphoramidites useful for forming phosphodiester linkages with hydroxyl groups, as well as methods for their use in nucleic acid synthesis on solid substrates, are described, for example in Zhang et al., 1991, Nucl. Acids Res. 19:3929–3933 and Durand et al., 1990, Nucl. Acids Res. 18:6353–6359. Other useful linkers are commercially available.

The polynucleotide sandwich arrays according to the invention can be used in virtually any assay in which hybridization is desirable. For example, the polynucleotide sandwich arrays of the invention are useful for all three formats of sequencing by hybridization, as well as the myriad other hybridization arrays performed with arrays of polynucleotide probes described in the art.

Use of the sandwich arrays of the present invention contemplates the use of either probe polynucleotides or target nucleic acids that are capable of generating a signal when appropriately hybridized to the array. The probe polynucleotides or target nucleic acids may be labeled. Virtually any label that produces a detectable, quantifiable signal and that is capable of being immobilized on a substrate or attached to a polynucleotide can be used in conjunction with the arrays of the invention. Suitable labels include, by way of example and not limitation, radioisotopes, fluorophores, chromophores, chemiluminescent moieties, etc. The label can be attached to any part of the probe or target polynucleotide, including the free terminus or one or more of the bases. Preferably, the position of the label will not interfere with hybridization, detection or other post-hybridization modifications of the labeled polynucleotide. Suitable methods of making labeled polynucleotides are well known in the art.

Due to their ease of detection, polynucleotides labeled with fluorophores are preferred. Fluorophores suitable for labeling polynucleotides are described, for example, in the Molecular Probes catalog (Molecular Probes, Inc., Eugene OR 97402-9144), and the references cited therein. Methods for attaching fluorophore labels to polynucleotides are well known, and can be found, for example in Goodchild, 1990, supra. A preferred fluorophore label is the carboxylic acid of tetramethyl rhodaimine (TAMRA dye), which is available from Molecular Probes.

Alternatively, the probes or targets may be labeled by any other technique known in the art. Preferred techniques include direct chemical labeling methods and enzymatic labeling methods, such as kinasing and nick-translation.

In use, the individual arrays immobilized on substrates 12, 14 (FIG. 1) composing the sandwich array 30 are disposed facing each other, separated by one or more spacer elements 16, 18 (FIGS. 2–7). The substrates 12, 14 containing the arrays composing the sandwich array 30 may be held together by a holder element 10, discussed in more detail infra. The substrates 12, 14 containing the arrays and the spacer elements 16, 18 define one or more reaction chambers 20 (in the following discussion, the singular "chamber" is intended to represent "chamber or chambers"). Hybridization solution containing the target nucleic acid or probe polynucleotide is placed in contact with the arrays, preferably by introduction into the chamber 20. Preferably, the solution is introduced into the chamber 20 by capillary action, entering through gaps 26 in the spacers 16, 18 at the top of the sandwich array 30; in this embodiment, the bottom of the chamber is left open to allow air to flow out of the chamber. The target nucleic acid in the hybridization solution may be labeled or unlabeled, depending on the particular assay (for example, format II vs. format III SBH).

The hybridization solution is contacted with the arrays under conditions which allow discrimination between perfectly complimentary hybrids and hybrids containing one or more mismatches in the informational content of the probes. The actual hybridization conditions used will depend upon, among other factors, the G+C content of the sequence of interest and the lengths of the immobilized polynucleotides comprising the array. Hybridization conditions useful for discriminating between perfect complements and mismatches for a variety of hybridization arrays have been described in the art. For example, hybridization conditions useful for discriminating complimentary and mismatched hybrids in a variety of SBH and other applications are described in U.S. Pat. No. 5,525,464 to Drmanac et al., WO 95/09248 and WO 98/31836. A particularly detailed discussion of the theoretical and practical considerations involved in determining hybridization conditions, and including a discussion of the advantages of low-temperature washing steps, may be found in WO 98/31836, particularly pages 50–62. Additional guidance may be found in Harmes and Higgins, Nucleic Acid Hybridization: A Practical Approach, 1985, IRL Press, Oxford, England.

Following contact under conditions appropriate to the particular assay, the solution is removed. In the capillary system, the solution may preferably be removed by blotting with a suitable absorbent material. The arrays are then optionally washed, typically under moderate to high stringency conditions, to remove unhybridized target. Washing is preferably accomplished by flowing a wash solution or series of wash solutions through the chamber. Preferably, the arrays are then separated and read using standard devices and methods appropriate to the chosen labeling method, such devices and methods being well known in the art. For example, if the target is labeled, the arrays can be scanned or otherwise analyzed for detectable assay signal, and the signal from each labeled spot, or alternatively from all spots, quantified. In a particular embodiment, the arrays may be read on a PE Applied Biosystems Bioscan Unit 9002 or a General Scanning Scanarray 3000. Only those spots where hybridization occurred will produce a detectable assay signal, and spots containing perfectly complementary hybrids are expected to produce more intense assay signals than spots containing mismatched hybrids.

Alternatively, the arrays may be separated at any other time after hybridization. For example, the individual arrays can be separated in order to remove the hybridization solution and then optionally washed separately. The arrays may also be separated at any point during the optional washing phase. In some applications, the arrays may not need to be separated at all, and may be read directly in the sandwich configuration.

While use of the sandwich array is illustrated utilizing a labeled target nucleic acid, those of skill in the art will recognize that the arrays of the invention are also useful in assays employing unlabeled target nucleic acids, such as assays employing the principles of format III SBH. Hybrids may also be detected using reagents specific for hybrids, such as ethidium bromide or other fluorophores specific for double-stranded DNA. The only requirement is that some component of the particular assay generate a detectable signal at spots where hybridization occurs.

A variety of methods of maintaining the assembly of substrates and spacers in a desired configuration to form the desired chambers have been used, each method having accompanying disadvantages. One method involves the taping together of the substrates. However, such tape may seal the bottom of the chamber, interfering with the desired escape of air therefrom which would facilitate filling as discussed above. Moreover, the tape may be difficult to remove and/or may leave a residue on the substrate upon separation of the substrates for separate reading.

Another method of maintaining the desired configuration of substrates and spacers involves the clamping together of the substrates with a clamping device. However, the presently used clamping devices include such devices as binder clips which may apply a force to the substrate which is great enough to potentially damage the substrate material. Moreover, such clamping devices typically interfere with storage or shipping of the sandwich array and therefore must be removed and replaced with an appropriate alternative for storage and/or shipping.

Therefore, in addition to the sandwich arrays of the present invention, a device is provided for holding together a pair of substrates of a sandwich array and also for serving other desired functions desired during the use of the sandwich array. This holder is especially useful with sandwich arrays comprising two arrays prepared on, for example, glass slides. In accordance with this embodiment of the principles of the present invention, a clamping bar 10 (FIGS. 2–7) is provided for maintaining together substrates 12, 14 (FIG. 1) of a sandwich array. As may be appreciated with reference to FIG. 1, each substrate 12, 14 is preferably provided with respective spacers 16, 18; however, the spacers may also be present on only one of the substrates. Spacers 16, 18 may be formed in any desired manner. For example, spacers 16, 18 may be in the form of TEFLON masks formed over a planar surface of each of substrates 12, 14 and configured such that upon positioning substrates 12, 14 adjacent to each other and pressing together spacers 16, 18, a desired number of chambers 20 are formed with walls defined by substrates 12, 14 and spacers 16, 18. In an alternative preferred embodiment, the spacers 16, 18 are made from a solution of silicone (e.g., household silicone glue and seal paste) in an appropriate solvent (such solvents are well known in the art). This solution of silicone grease is applied between the subarrays to form lines which, after the solvent evaporates, act as spacers 16, 18.

In order to fill chambers 20, substrates 12, 14 should be maintained in a predetermined position with respect to each other. Accordingly, clamping bar 10 is provided over the bottom edges 13 of substrates 12, 14 to maintain substrates 12, 14 adjacent to each other to form chambers 20 therebetween. The chambers 20 are filled through gaps 26 in the spacers 16, 18 at top edges 15 of substrates 12, 14. Clamping bar 10 preferably has a width W which extends across the entire width of bottom edges 13 of substrates 12, 14 to minimize any potential leakage of solution being filled within chambers 20.

As may be appreciated with reference to the cross-sectional view of FIG. 4A, clamping bar 10 has a substantially flat-bottomed 28 U-shaped cross-section. The clamping arms 22, 24 of clamping bar 10 are biased together such that upon insertion of substrates 12, 14 therebetween clamping arms 22, 24 exert a sufficient force to maintain substrates 12, 14 together to form chambers 20 therebetween, thereby forming sandwich array 30. It will be appreciated that arms 22, 24 are formed from a sufficiently flexible, resilient material such that respective free ends 32, 34 thereof do not damage substrates 12, 14 despite the clamping force exerted thereon. In a neutral configuration, without a force applied to arms 22, 24 and without substrates 12, 14 positioned therebetween, free ends 32, 34 preferably are spaced apart to facilitate insertion of substrates 12, 14 therebetween. Clamping bar 10 may be inserted over bottom edges 13 either by a sliding movement in a direction along bottom edges 13 or by a movement substantially perpendicular to bottom edges 13.

In an alternative embodiment shown in FIG. 4B, free ends 32, 34 may be curved away from substrates 12, 14 so that a substantially convex surface 36, 38 of clamping arms 22', 24' presses against respective substrates 12, 14 to hold substrates 12, 14 together to form array 30'. The convex shape of surfaces 36, 38 further minimizes the risk of arms 22', 24' damaging substrates 12, 14. Moreover, such convex shape further separates free ends 32, 34 from each other, thus further facilitating insertion of substrates 12, 14 therebetween.

The provision of clamping bar 10 with a substantially flat bottom wall 28 permits sandwich array 30 to be supported by clamping bar 10 in a substantially upright or vertical position, as may be appreciated with reference to FIG. 4. Thus, additional clamping devices for maintaining the orientation of sandwich array 30 may not be necessary. If such additional orientation maintaining clamping devices are used nonetheless, then clamping bar 10 serves the further function of protective substrates 12, 14 from such orientation maintaining clamping device.

Figure 2A:
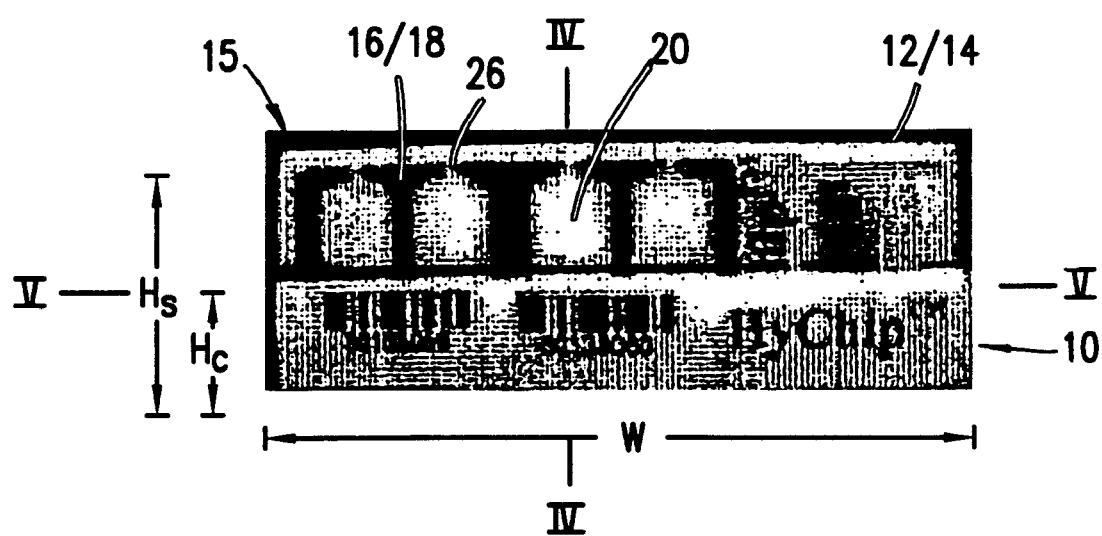
FIG. 2 is a photographic (A) or drawn (B) plan view of a sandwich array with a pair of substrates coupled together with a clamping bar formed in accordance with the principles of the present invention.
Figure 2B:
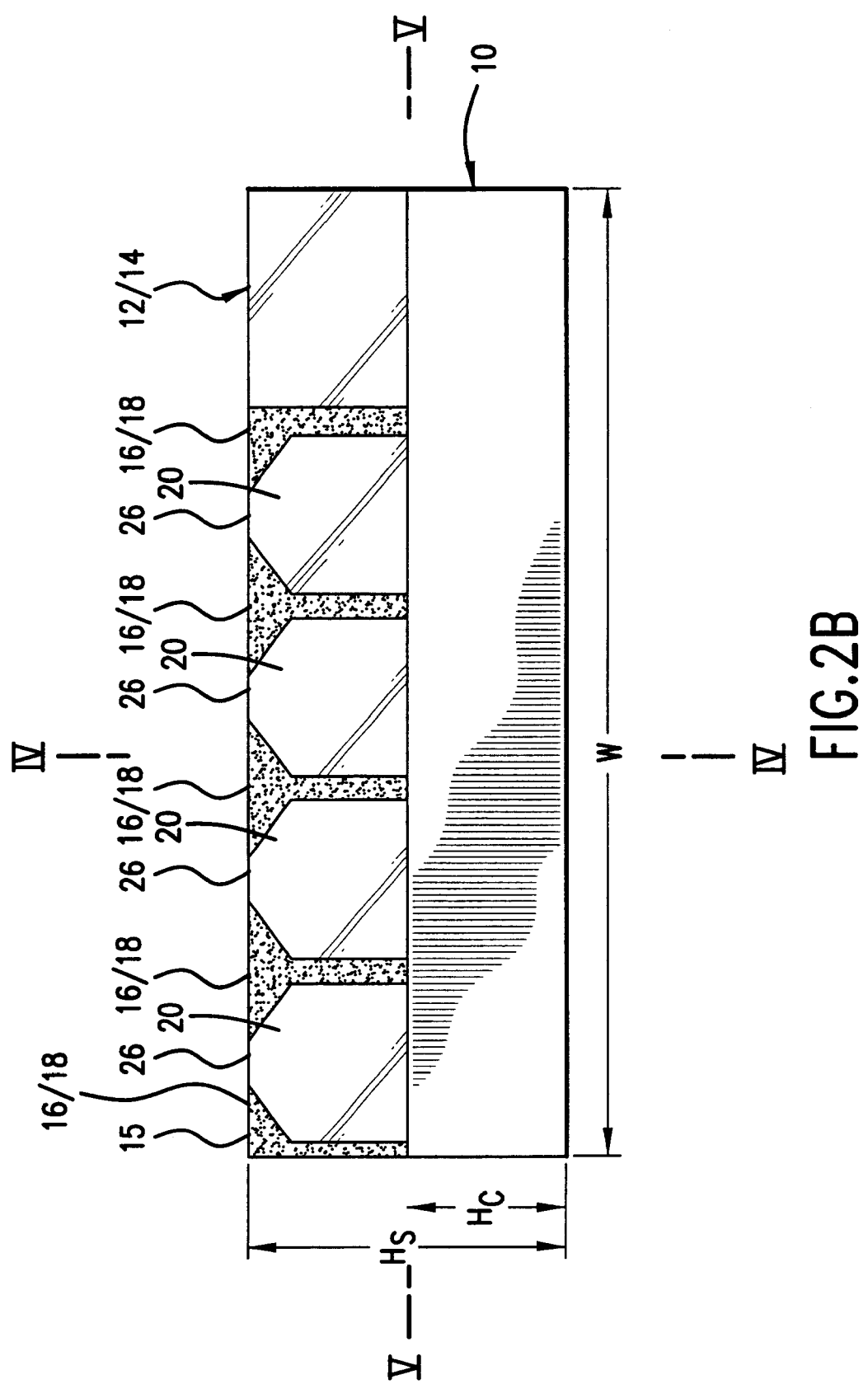
Figure 3:
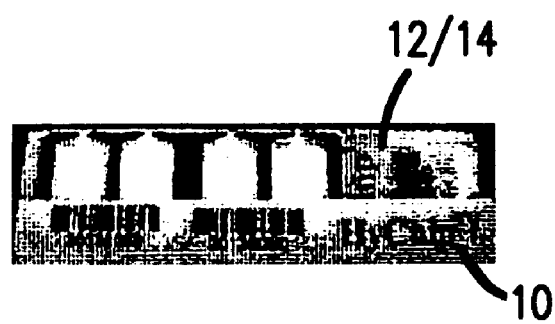
FIG. 3 is a perspective view of the sandwich array and clamping bar of FIG. 2.
Figure 6:
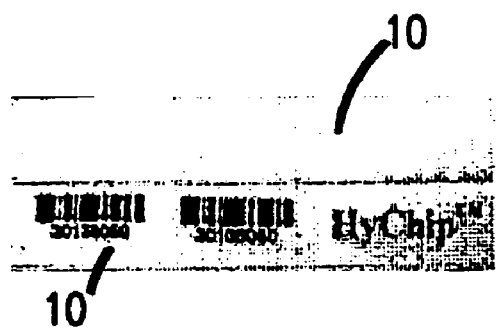
FIG. 6 is a plan view of a sandwich array similar to that of FIG. 2, but with two clamping bars formed in accordance with the principles of the present invention positioned thereon for storage or shipping of the sandwich array.
Figure 7:
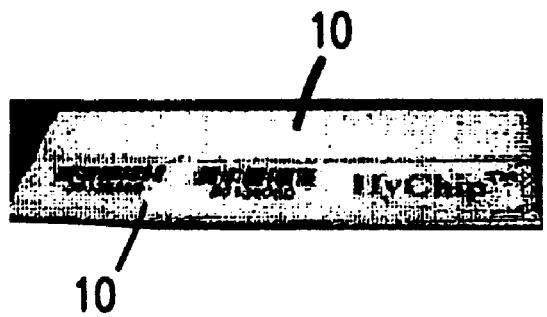
FIG. 7 is a perspective view of the sandwich array and clamping bars of FIG. 6.

As may be appreciated with reference to FIGS. 2 and 3, the height $H_c$ of clamping arms 22, 24 preferably is selected as one half the height $H_s$ of substrates 12, 14. Thus, the use of a second clamping bar 10 across top edges 15 of substrates 12, 14, as shown in FIGS. 6 and 7, causes arms 22, 24 of clamping bars 10 to substantially completely cover the walls of substrates 12, 14. Array 30, with a clamping bar 10 across each of the top and bottom edges as shown in FIGS. 6 and 7, is thus securely packaged for storage and/or shipping.

Clamping bars 10 are formed from a resilient material, and therefore are easily removable from substrates 12, 14 to permit separation of substrates 12, 14 for individual readings therefrom.

An exemplary material from which clamping bar 10 may be formed is a slider bar from a standard report cover formed of two plastic sheets held together along a long side thereof by the slide bar. However, any other construction which satisfies the above-described principles of the present invention may be used instead.

Example: Preparation and use of a Sandwich Array of Polynucleotides

Preparation of the Arrays

Two arrays of polynucleotides are generated using the surfaces of two glass slides as substrates. Each slide contains four replicate arrays of polynucleotides. The polynucleotides used are 8 bases long, with an information content corresponding to all possible 5-base sequences. The polynucleotides all have the structure 5'-H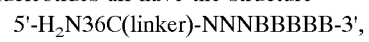

where:

H₂N36C(linker) is a standard, commercially available 36 carbon linker element;

N represents a degenerate position generated by synthesizing the polynucleotide with an equimolar mixture of all four bases according to standard methods (i.e., each location on the array contained a mixture of polynucleotides degenerate at the N positions); and B represents any one of the four bases (i.e., each location on the array contained a mixture of polynucleotides identical at the B positions).

Figure 1B:
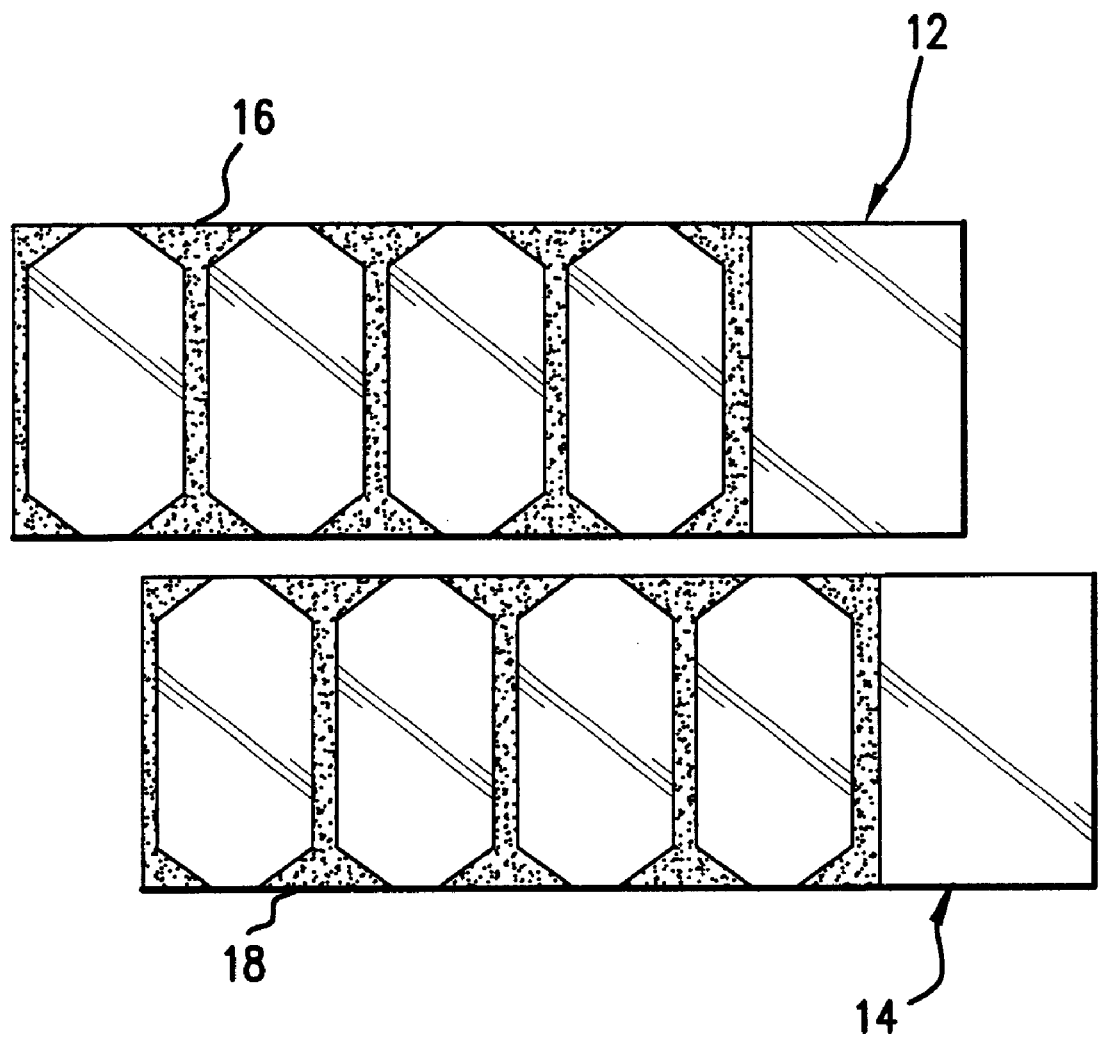

Glass slides having TEFLON spacers as shown in FIG. 1 are prepared for attachment of the polynucleotides of the array by generating isothiocyanate groups (—N=C—S) on the surface of the slide. The slide is derivatized with isothiocyanate groups according to the following protocol:

(1) Soak glass slide in 1 M HCl for 16 hr. (Alternatively, soak in 1 M nitric acid for 3 hr.) Rinse thoroughly with deionized water, followed by acetone. Allow to air dry.

(2) Soak slide in hexane, acetone, and methanol, respectively, for 10 min each. Air dry when done. The slide must be completely dry before proceeding to the next step.

(3) Prepare a solution containing 2% aminopropyltriethoxy silane in 95% acetone:water in a plastic container and let stand 10 min to activate. Submerge slide in this silane solution for about 2 min and immediately rinse with acetone. Wash slide with 3 consecutive acetone washes. Allow to completely air dry.

(4) Cure slides by baking in a dry incubator at 98° C. for 45 min. Remove from incubator and allow to cool for at least 10 min.

(5) Dissolve 1,4-phenylene diisothiocyanate (PDC) in a 10% solution of pyridine:dimethyl formamide to yield a final concentration of 0.2% PDC. Submerge the slide in the PDC solution and incubate for 2 hr at room temperature. Remove the slide and wash by submerging in methanol for 5 min, followed by two successive baths of acetone for 5 min each. Allow slide to air dry.

For each spot of the array, small volumes of polynucleotides mixtures containing 50 µM of the particular degenerate polynucleotide pool for that spot are prepared. These mixtures are then spotted onto the prepared slide using a robotic pin spotting device. The spotted polynucleotides covalently bond to the surface of the slide through a bond between the cyanate molecule on the slide and the 5' amine of the polynucleotide. Each of the arrays contains four replicates of one half of the full set of polynucleotides of 5-mer length, so that the two arrays together contain four replicates of the full set of 5-mers.

Use of the Arrays

The two arrays are placed facing each other, with their respective spacers aligned. The arrays are held together by a clamping bar. This arrangement creates four chambers defined by the spacers and the glass slides, and the two arrays in each chamber define a complete set of polynucleotides of 5-mer information content. Each chamber has an opening at the top and bottom. Hybridization solution containing a target nucleic acid, a fluorescently labeled 5-mer polynucleotide, ligase, and appropriate hybridization buffer components is added to the chambers of sandwich array through the opening in the top of the chamber. Each chamber receives a hybridization solution containing a different fluorescently labeled 5-mer polynucleotide. The hybridization solution is maintained in contact with the arrays for an appropriate length of time at an appropriate temperature, then drained through the bottom opening using absorbent material. After hybridization, the arrays are washed by flowing appropriate wash solutions through the chambers. After washing, the arrays are separated and allowed to air dry. The separated arrays are then read by detecting those spots having labeled probes ligated thereto. The data so generated are used in determining the sequence of the target polynucleotide.

The present invention is not to be limited in scope by the exemplified embodiments which are intended as illustrations of single aspects of the invention The foregoing specification and accompanying drawings is considered to be sufficient to enable one skilled in the art to broadly practice the invention. Indeed, various modifications of the above-described means for carrying out the invention which are obvious to those skilled in the relevant arts are intended to be within the scope of the following claims. All patents, patents applications, and publications cited herein are hereby incorporated by reference in their entireties for all purposes.

What is claimed:

1. A sandwich array comprising:

a first substrate comprising a spatially addressable array of biological compounds immobilized thereon;

a second substrate comprising a spatially addressable array of compounds immobilized thereon; and a spacer disposed between the first and second substrates thereby forming one or more chambers between the substrates;

wherein the first and second substrates are positioned with respect to each other such that when an assay solution is applied to the sandwich array, the assay solution contacts at least one compound from the first array and at least one compound from the second array.

2. The sandwich array of claim 1, wherein the substrates and the spacer form a plurality of chambers.

3. The sandwich array of claim 1, wherein at least one of the substrates comprises a glass slide or a plastic sheet.

4. The sandwich array of claim 1, wherein the arrays are two-dimensional arrays.

5. The sandwich array of claim 1, wherein the immobilized compounds are polynucleotides.

6. The sandwich array of claim 5, wherein the polynucleotides are covalently attached to the substrate, optionally by way of a linker.

7. The sandwich array of claim 6, wherein the polynucleotide is covalently attached via a terminal nucleotide.

8. The sandwich array of claim 1, wherein each array comprises 10 to $10^6$ unique compounds.

9. The sandwich array of claim 6, wherein each immobilized polynucleotide is independently 6 to 20 nucleotides in length.

10. The sandwich array of claim 6, wherein each immobilized polynucleotide is 6–20 nucleotides is length.

11. The sandwich array of claim 1, wherein at least one of the arrays comprises all possible polynucleotides 6–10 nucleotides in length.

12. The sandwich array of claim 1, wherein at least one of the arrays comprises a subset of polynucleotides 6–10 nucleotides in length.

13. The sandwich array of claim 5, wherein at least one spatial address has immobilized thereto a mixture of polynucleotides.

14. The sandwich array of claim 13, wherein the mixture is of the formula: $N_x B_y N_z$, wherein N represents any of the four bases and varies for the polynucleotides in a given mixtures, B represents any of the four bases but is the same for each of the polynucleotides in a given mixture, and x, y, and z are integers.

15. The sandwich array of claim 13, wherein each spatial address of at least one array immobilized thereto a mixture of polynucleotides of the formula: $N_xB_yN_z$, wherein N represents any of the four bases and varies for the polynucleotides in a given mixtures, B represents any of the four bases but is the same for each of the polynucleotides in a given mixture, and x, y, and z are integers.

16. The sandwich array of claim 1 further comprising:
a first clamping bar comprising first and second arms spaced apart when in a neutral configuration to permit insertion of said first and second substrates there between, said clamping bar arms being biased together to clamp said first and second substrates there between to maintain said first and second substrates in a desired position with respect to each other.

17. The sandwich array of claim 16, wherein said first and second substrates and said clamping bar have the same widths.

18. The sandwich array of claim 16, wherein said first and second substrates have a first height and said clamping bar arms have a second height, said second height being half of said first height.

19. The sandwich array of claim 16, wherein:
said first and second substrates have bottom edges and top edges,
said first clamping bar is positioned over said bottom edges of said first and second substrates; and
said sandwich array further comprises a second clamping bar with first and second clamping arms positioned over said top edges of said first and second substrates.

20. The sandwich array of claim 19, wherein:
said first and second substrates have a first height;
said arms of said first and second clamping bars have a second height; and
said second height is half of said first height;
whereby said substrate is covered by said arms of said first and second clamping bars when said first and second clamping bars are positioned respectively over said top and bottom edges of said first and second substrates.

21. The sandwich array of claim 1, wherein said biological compounds are synthetic polynucleotides.

* * * * *

UNITED STATES PATENT AND TRADEMARK OFFICE
CERTIFICATE OF CORRECTION

PATENT NO. : 6,268,210 B1
DATED : July 31, 2001
INVENTOR(S) : Baier et al.

Page 1 of 1

It is certified that error appears in the above-identified patent and that said Letters Patent is hereby corrected as shown below:

Column 16,
Line 53, replace "nucleotides" with -- nucleotide --.
Line 56, replace "is" with -- in --.

Signed and Sealed this

Twenty-first Day of May, 2002

Attest:

JAMES E. ROGAN
*Attesting Officer*     *Director of the United States Patent and Trademark Office*